United States Patent [19]

Kelly

[11] Patent Number: 5,700,393
[45] Date of Patent: Dec. 23, 1997

[54] LIQUID CRYSTALLINE COMPOUNDS

[75] Inventor: Stephen Kelly, Beverley, England

[73] Assignee: Rolic AG, Basel, Switzerland

[21] Appl. No.: 687,869

[22] Filed: Jul. 26, 1996

[30] Foreign Application Priority Data

Jul. 28, 1995 [CH] Switzerland ............... 2220/95
May 9, 1996 [EP] European Pat. Off. ........... 96107333

[51] Int. Cl.$^6$ ............ C09K 19/30; C09K 19/52; C09K 19/20; C07C 69/76
[52] U.S. Cl. .............. 252/299.63; 252/299.01; 252/299.6; 252/299.61; 252/299.64; 252/299.65; 252/299.66; 252/299.67; 560/60; 560/76; 560/102; 560/65; 568/647
[58] Field of Search ............ 252/299.65, 299.67, 252/299.01, 299.63, 299.6, 299.61, 299.66, 299.64; 560/76, 102, 60, 65; 568/647, 648

[56] References Cited

U.S. PATENT DOCUMENTS

| | | | |
|---|---|---|---|
| 4,877,220 | 10/1989 | Praefcke et al. | 252/299.61 |
| 5,538,768 | 7/1996 | Marden et al. | 428/1 |
| 5,567,349 | 10/1996 | Kelly et al. | 252/299.01 |
| 5,593,617 | 1/1997 | Kelly et al. | 252/299.67 |

FOREIGN PATENT DOCUMENTS

WO 95/16007  6/1995  WIPO.

OTHER PUBLICATIONS

Derwent Abstract 95-216450/29 (Jun. 1995).

*Primary Examiner*—C. H. Kelly
*Attorney, Agent, or Firm*—Mark E. Waddell; Bryan Cave LLP

[57] ABSTRACT

The present invention is concerned with photo cross-linkable liquid crystalline compounds of the general formula

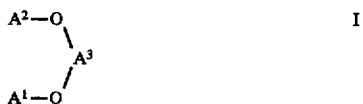

wherein $A^1$ and $A^2$ each are a cross-linkable mesogenic residue; and $A^3$ is (R,R)- or (S,S)-trans-1,2-cyclohexyl-diyl, liquid crystalline mixtures which contain such compounds and their use in the cross-linked state as optical components.

10 Claims, No Drawings

LIQUID CRYSTALLINE COMPOUNDS

The present invention is concerned with photo cross-linkable, optically active compounds, liquid crystalline mixtures which contain such compounds as well as their use in the cross-linked state as optical components.

Photo cross-linkable liquid crystals, which are provided with a suitable amount of a photoinitiator, can be oriented on a substrate or in a cell by suitable orienting layers or in a field and then in this state can be cross-linked by irradiation with light of a suitable wavelength. The structure thereby produced is preserved even at high temperatures. Thus, optical components such as, for example, wave guides, optical grids and filters, piezoelectric cells and cells having non-linear optical (NLO) properties, electro-optical devices, etc. can be produced. Such optical components can be used, for example, in cells for frequency doubling (SHG) or in color filters.

Further properties such as, for example, the birefringence, the refractive index, the transparency, etc. must fulfill different requirements depending on the field of use. For example, materials for color filters, polarizers, ½ plates, etc. should produce a small pitch for circularly polarized light.

The photo cross-linkable liquid crystals must have a good chemical and thermal stability, good solubility in usual solvents and a good stability towards electric fields and electromagnetic radiation. They should have a suitable mesophase in a temperature range from about 25° C. to about +100° C., especially from about 25° C. to about +80° C.

Chiral nematic (cholesteric) liquid crystals in the homogeneously orientated state (Grandjean texture) reflect light essentially only in a wavelength range which is dependent on the wavelength of the helical pitch. The spectral width of this reflected light can be varied by suitable choice of the liquid crystal. The reflected light is completely circularly polarized. The direction of rotation of the reflected light depends on the direction of rotation of the cholesteric helical structure. The oppositely circularly polarized light is transmitted unimpaired. These properties can be used for the production of optical filters, polarizers, analyzers, etc. When such cholesteric mixtures contain photochemically oligomerizable or polymerizable components, then these components can be cross-linked by irradiation with light. The liquid crystalline structure of these mixtures is thereby stabilized or even frozen. Thus, color filters, ½ plates, optical retarders, polarizers, etc. can be produced in the solid state.

Since liquid crystals are usually used as mixtures of several components, it is important that the components have a good miscibility with one another. Mixtures consisting of photo cross-linkable liquid crystals and non-photo cross-linkable components, which lead to optical activity in mixtures, allow the non-cross linked components to relax and thereby decrease the stability of the network. Conventional optically active photochemically oligomerizable or polymerisable additives have the center of chirality in the spacers between the photo cross-linkable group and the core of the molecule. This requires an expensive and complicated synthesis. The twisting capacity of these compounds is relatively small.

There is accordingly the need to produce, especially for use in optical filters, photochemically oligomerizable or polymerizable optically active compounds which have a large twisting capacity. Thus, they can be admixed in liquid crystalline mixtures in small concentrations in order to produce the desired pitch without influencing the clearing point or other physical properties of the mixture too severely. Moreover, they should be readily accessible from starting materials which are known or which are commercially available. Furthermore, mixtures which contain such optically active photo cross-linkable compounds should be structurally as domain-free as possible and should also have an excellent thermal stability and long-term stability in the cross-linked state.

The present invention now provides compounds which are outstandingly suitable as single components or as components of such liquid crystal mixtures. The compounds of the present invention have general formula I

wherein $A^1$ and $A^2$ each are a cross-linkable mesogenic residue; and $A^3$ is (R,R)- or (S,S)-trans-1,2-cyclohexyl-diyl.

Since the compounds of formula I in accordance with the invention or mixtures containing such compounds have a mesophase, they can, prior to the cross-linking, be oriented on an orienting layer by the application of an electric or magnetic field. A uniform layer is produced in this manner.

Preferably, the mesogenic residues $A^1$ and $A^2$ each are a residue of general formula II

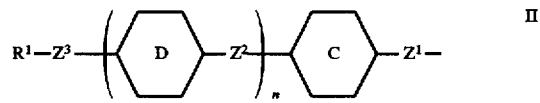

wherein rings C and D each independently are selected from the group consisting of pyridine-2,5-diyl, pyrimidine-2,5-diyl, trans-1,4-cyclohexylene, trans-1,3-dioxane-2,5-diyl, 1,4-phenylene, and 1,4-phenylene substituted with one or more halogen, methyl or cyano;

$Z^1$ is selected from the group consisting of $CH_2)_m$—, —CO—, —$(CH_2)_m$CO— and —$(CH_2)_m$OOC—;

$Z^2$ is selected from the group consisting of a single bond, —$CH_2CH_2$—, —$CH_2O$—, —$OCH_2$—, —COO—, —OOC—, —$(CH_2)_4$—, —$O(CH_2)_3$— and -$(CH_2)_3O$—;

$Z^3$ is selected from the group consisting of —$(CY_2)_m$—, —$O(CY_2)_m$—, —$(CY_2)_mO$—, —$(CY_2)_mCOO$—, —$(CY_2)_mOOC$—, —$Si[(CH_3)_2]O)_m$—, —$OCH_2(Si[(CH_3)_2]O)_m Si[(CH_3)_2]CH_2O$— and —$NHCH_2(Si[(CH_3)_2]O)_m Si[(CH_3)_2]CH_2NH$—;

Y is hydrogen or fluorine;

n is 0, 1 or 2;

m is a whole number of 1 to 16; and $R^1$ is a cross-linkable group selected from the group consisting of $CH_2$=CH—, $CH_2$=CH—COO—, $CH_2$=C($CH_3$)—COO—, $CH_2$=C(Cl)—COO—, $CH_2$=C(Ph) —COO—, $CH_2$=CH—COO—Ph—, $CH_2$=CH—CO—NH—, $CH_2$=C($CH_3$)—CONH—, $CH_2$=C(Cl)—CONH—, $CH_2$=C(Ph)—CONH—, $CH_2$=C(COOR')—$CH_2$—COO—, $CH_2$=CH—O—, $CH_2$=CH—OOC—, Ph—CH=CH—, $CH_3$—C(=NR')—, cis,trans HOO—CR'=CR'—COO—,

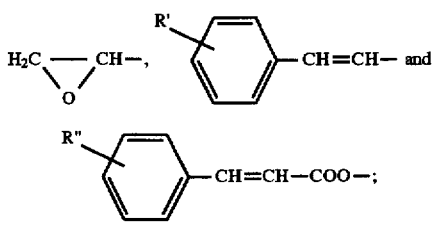

Ph is phenyl;

R' is lower alkyl; and

R" is selected from the group consisting of methyl, methoxy, cyano and halogen;

wherein $R^1$—$Z^3$— contains no —O—O— or —N—O— groups.

Compounds of formula I in which the two mesogenic residues $A^1$ and $A^2$ are the same are preferred.

Especially preferred are residues $A^1$ and $A^2$ of formula II in which rings C and D each independently are selected from the group consisting of unsubstituted 1,4-phenylene, fluoro-substituted 1,4-phenylene, pyridine-2,5-diyl, pyrimidine-2,5-diyl and trans-1,4-cyclohexylene; $Z^1$ is selected from the group consisting of -CH$_2$—, —CO— and —OOC—; $Z^2$ is selected from the group consisting of a single bond, —CH$_2$CH$_2$—, —CH$_2$O—, —OCH$_2$—, —COO— and —OOC—; and $Z^3$ is selected from the group consisting of —(CH$_2$)$_m$—, —(CH$_2$)$_m$O—, —(CH$_2$)$_m$COO— and —(CH$_2$)$_m$OOC—.

Preferably, the cross-linkable group $R^1$ is selected from the group consisting of CH$_2$=CH—COO—, CH$_2$=C(CH$_3$)—COO—, CH$_2$=C(Cl)—COO—, CH$_2$=C(Ph)—COO—, CH$_2$=CH—COO—Ph— CH$_2$=CH—CONH—, CH$_2$=C(CH$_3$)—CONH—, CH$_2$=C(Ph)—CONH—, CH$_2$=CH—O—, CH$_2$=CH—OOC—, cis,trans —HOO—CR'=CR'—COO—,

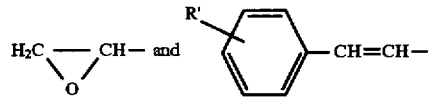

wherein R' is lower alkyl.

These are the residues which can be cross-linked photochemically after orientation of the compounds of formula I in a field.

Especially preferred groups $R^1$ are CH$_2$=CH—COO—, CH$_2$=C(CH$_3$)—COO—, CH$_2$=CH—O— and

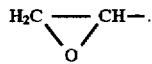

The terms used in the present application have the following meanings:

"1,4-phenylene substituted with one or more halogen, methyl or cyano" embraces in the present invention 1,4-phenylene mono- or multiply-substituted with fluorine, bromine, chlorine, methyl or cyano such as, for example, 2- or 3-fluoro-1,4-phenylene, 2,3-difluoro-1,4-phenylene, 2,6- or 3,5-difluoro-1,4-phenylene, 2- or 3-chloro-1,4-phenylene, 2,3-dichloro-1,4-phenylene, 2,6- or 3,5-dichloro-1,4-phenylene, 2- or 3-bromo-1,4-phenylene, 2- or 3-methyl-1,4-phenylene, 2- or 3-cyano-1,4-phenylene and the like;

"halogen" is fluorine, chlorine or bromine, especially fluorine;

"lower alkyl" is a straight-chain or branched alkyl group with 1 to 4 carbon atoms such as, for example, methyl, ethyl, propyl, butyl, i-propyl, i-butyl, tert.-butyl, especially methyl, ethyl, propyl or butyl.

The mesophase type of the compounds in accordance with the invention can be influenced by varying the rings in the side-chains $A^1$ and $A^2$. Thus, aromatic rings such as phenylene have the tendency to produce smectic phases, while saturated rings such as trans-1,4-cyclohexylene or trans-1,3-dioxane-2,5-diyl rings promote nematic tendencies.

Preferably, the mesogenic residues $A^1$ and $A^2$ signify a residue of formula II in which n is 1, i.e. a residue of formula II-a

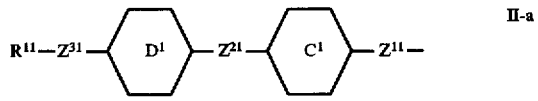

wherein rings $C^1$ and $D^1$each independently are selected from the group consisting of pyridine-2,5-diyl, pyrimidine-2,5-diyl, trans-1,4-cyclohexylene, 1,4-phenylene, and 1–4 phenylene substituted with fluorine;

$Z^{11}$ is —CH$_2$— or —CO—;

$Z^{21}$ is selected from the group consisting of a single bond, —CH$_2$O—, —COO— and —OOC—;

$Z^{31}$ is selected from the group consisting of —(CH$_2$)$_{m'}$—, —(CH$_2$)$_{m'}$·O—, —(CH$_2$)$_{m'}$·COO— and —(CH$_2$)$_{m'}$OOC—;

m' is a whole number of 3 to 12; and $R^{11}$ is selected from the group consisting of CH$_2$=CH—COO—, CH$_2$=C(CH$_3$)—COO—, CH$_2$=C—CH—O— and

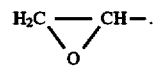

Especially preferred are compounds of the formulae

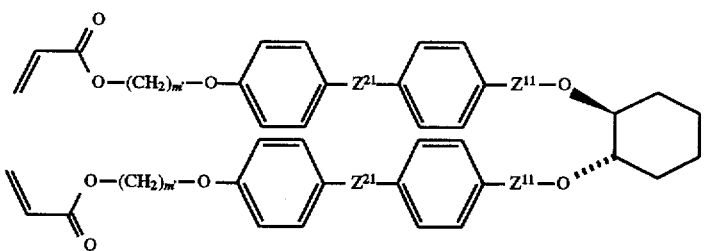

I-A

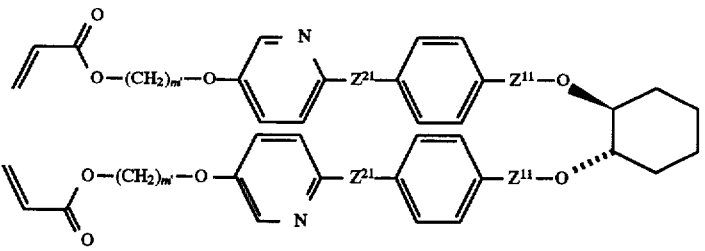

I-B

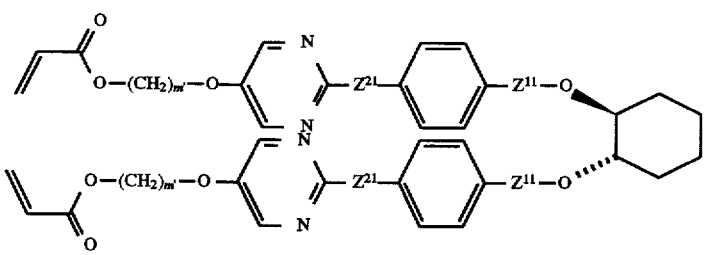

I-C

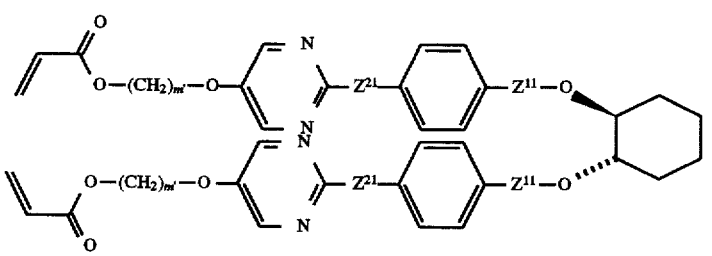

I-D

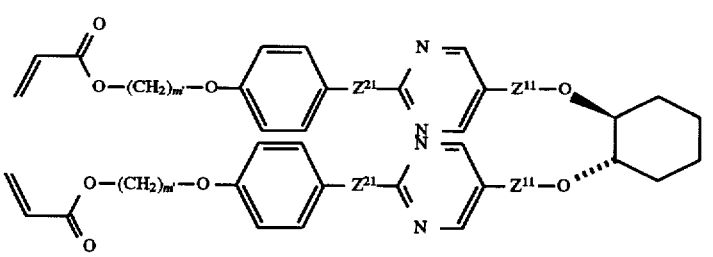

I-E wherein $Z^{11}$ is —CO— and $Z^{21}$ is a single bond or —COO—, especially —COO—, and m' is a whole number of 3 to 12, as well as the enantiomers of these compounds.

The compounds of formula I in which $A^1$ and $A^2$ are the same, are very readily synthesized, and can be produced, for example, analogously to the methods illustrated in Schemes 1 to 5. Thus, optically active diols can be reacted with (ω-acryloyloxyalkyloxy)-substituted carboxylic acids in a manner known per se. This esterification can be effected, for example, via the corresponding methylsulphonate in tetrahydrofuran or in the presence of N,N'-dicyclohexylcarbodiimide and 4-(dimethylamino)pyridine in dichloromethane or another suitable solvent such as chloroform. Optically active diols can also be reacted with (ω-acryloyloxyalkyloxy)-substituted benzyl tosylates in a Williamson etherification. This etherification can be effected, for example, at room temperature in the presence of potassium tert.-butylate in dimethoxyethane or another suitable solvent such as e.g. N,N'-dimethylformamide.

Compounds of formula I in which $A^1$ and $A^2$ are different can be produced by the mono-esterification of optically active diols with an (ω-acryloyloxyalkyloxy)-substituted carboxylic acid and subsequent esterification with a different (ω-acryloyloxyalkyloxy)-substituted carboxylic acid. The corresponding asymmetric diethers can also be produced in this two-stage process. The starting materials are known or are generally commercially available.

The reactions set forth in Schemes 1 to 5 are all effected in a manner known to those skilled in the art. Also, the reactions of Scheme I are described in U.S. Ser. No. 08/606,102.

Scheme 1
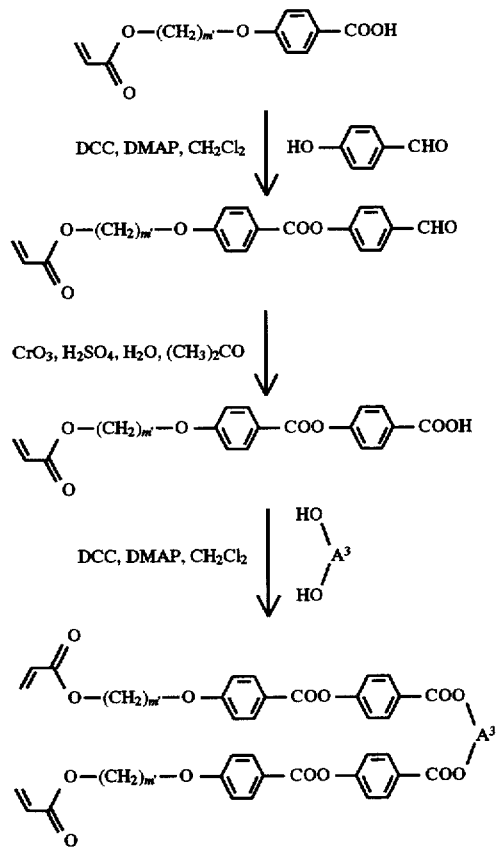
SCHEME 2
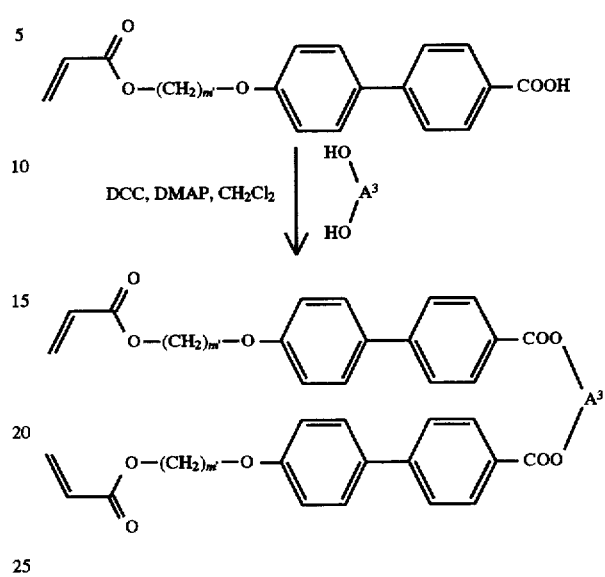
SCHEME 2
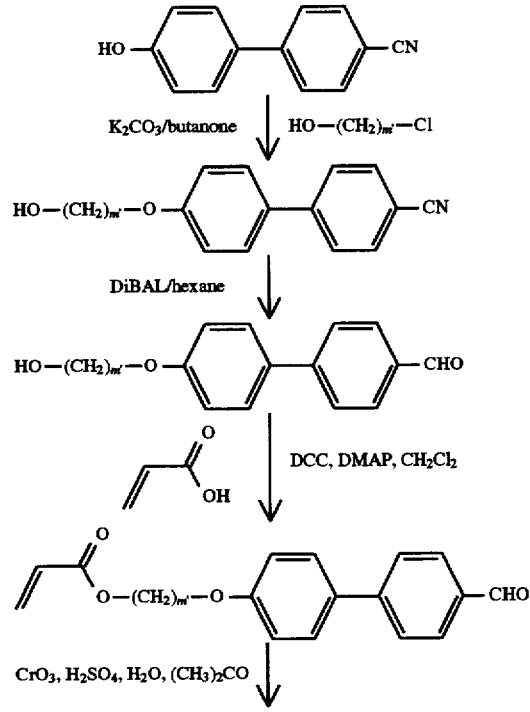
Scheme 3
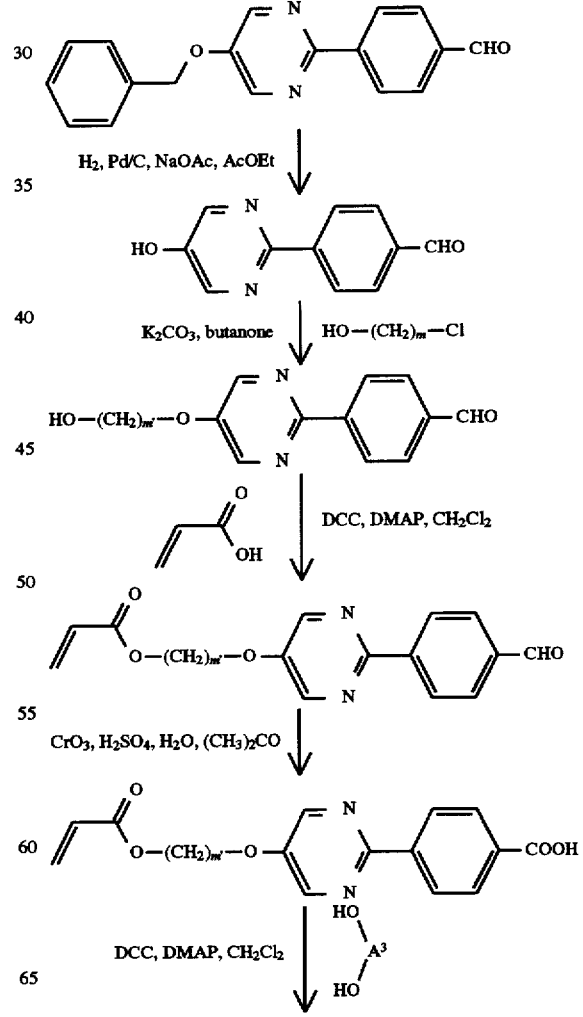

9
-continued
Scheme 3
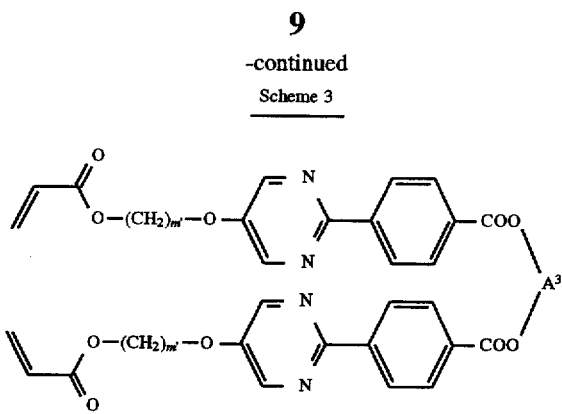
Scheme 4
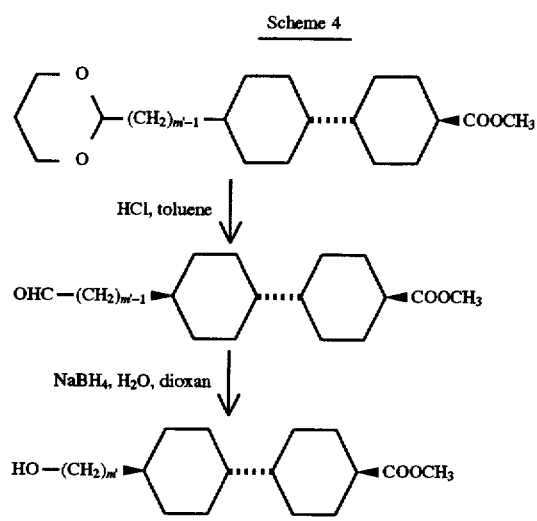
10
-continued
Scheme 4
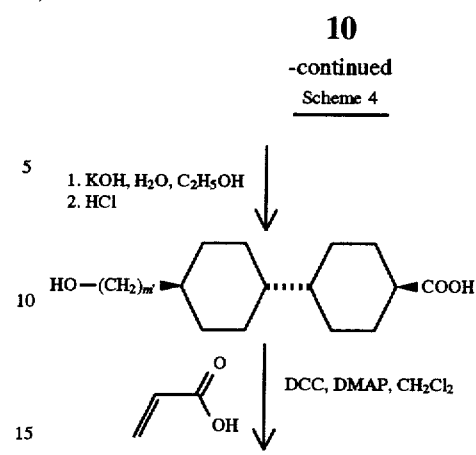
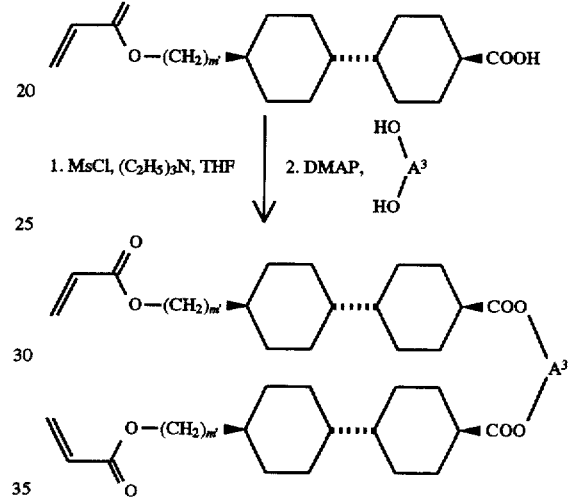
Scheme 5
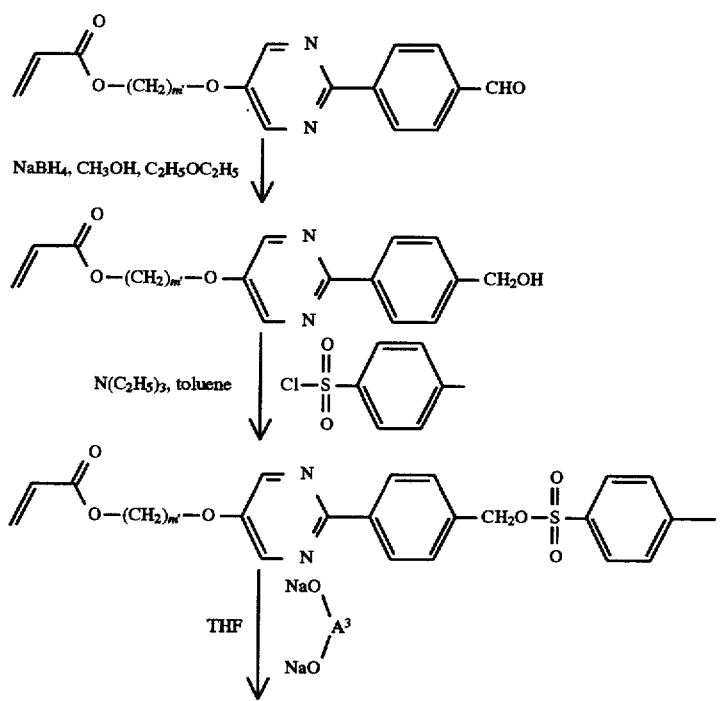

-continued
Scheme 5

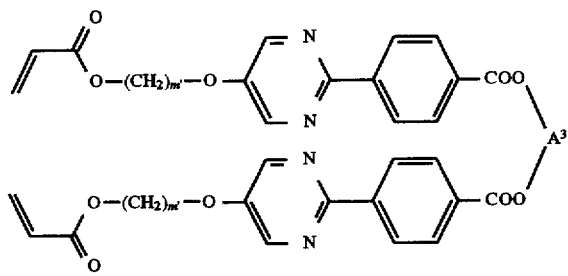

A small amount of BHT (2,6-di-tert.-butyl-4-methyl-phenol/"butylhydroxytoluene") is admixed in each step in order to stop undesired thermal cross-linkage.

The compounds of formula I are used as chiral dopants in liquid crystalline mixtures. These liquid crystalline mixtures contain at least one compound of formula I.

The content of chiral compounds of formula I in the liquid crystalline mixtures in accordance with the invention can vary in a wide range and can be, for example, about 0.1–30 wt. % and is determined essentially by the twisting capacity of the compounds and the desired pitch.

The liquid crystalline mixtures in accordance with the invention contain at least 2 components, of which at least one component is a compound of formula I. A second component and any additional components can be further compounds of formula I or other known liquid crystalline compounds having a photo cross-linkable group. Additional chiral components can also be present in the mixture.

The mixtures in accordance with the invention preferably contain, in addition to one or more compounds of formula I, one or more compounds from the group of compounds of the general formulae

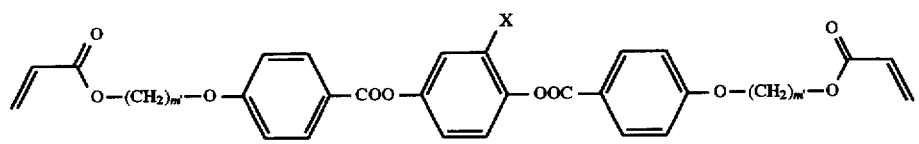

III

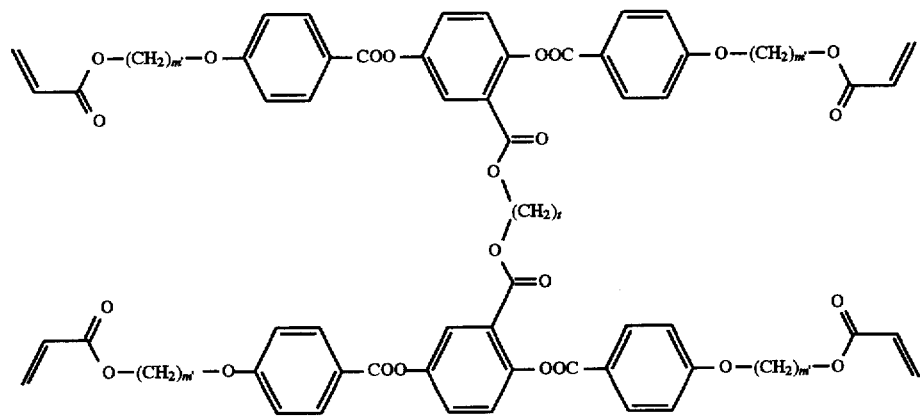

IV

-continued
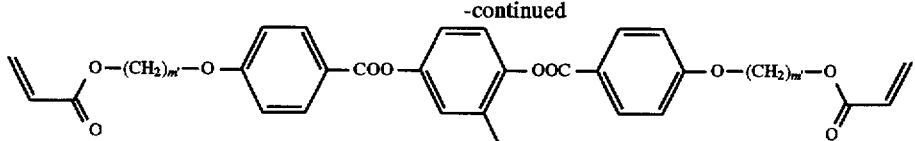
V
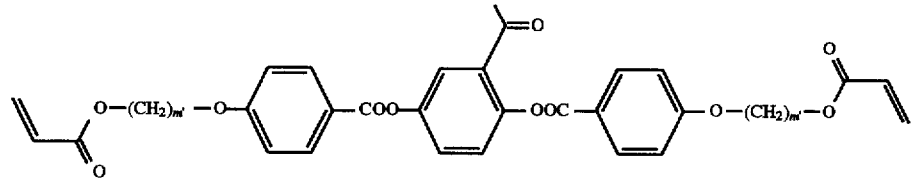
VI
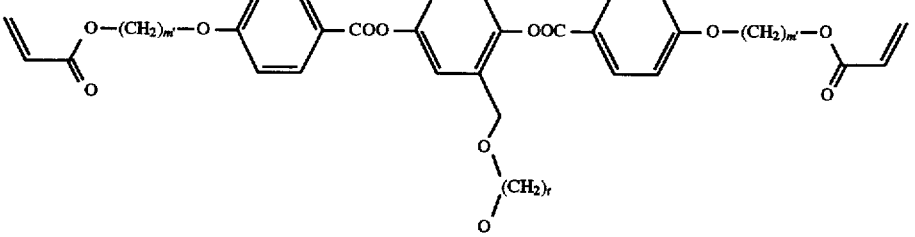
VII
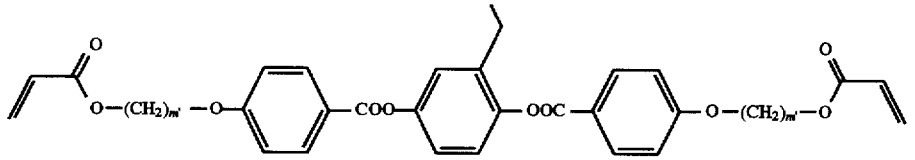
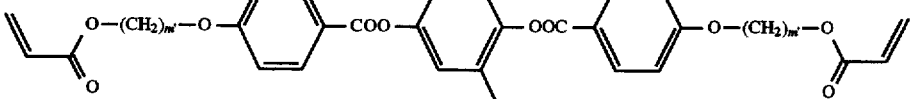
VIII
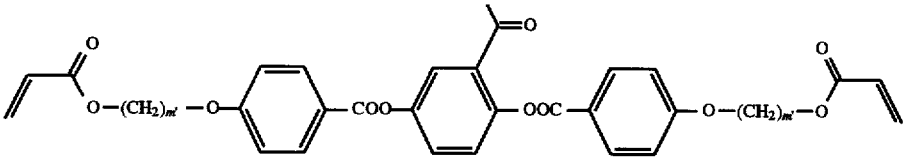

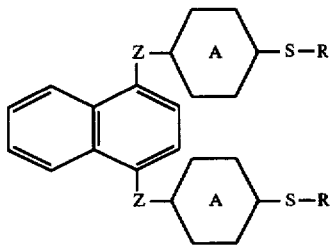

and

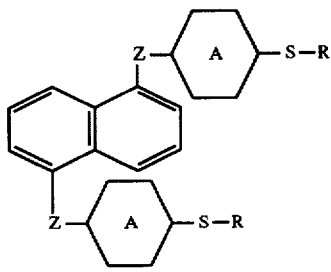

IX

X wherein

X is selected from the group consisting of hydrogen, fluorine, chlorine, bromine and methyl;

m' is a whole number of 4 to 12;

t is a whole number of 2 to 12;

Z is —OCH$_2$— or —OOC—;

A is 1,4-phenylene or 2- or 3-fluoro-1,4-phenylene;

S is —(CH$_2$)$_{m'}$, —(CH$_2$)$_m$O— or —O(CH$_2$)$_m$—; and

R is selected from the group consisting of CH$_2$=CH—COO—, CH$_2$=C(CH$_3$)—COO—, CH$_2$=CH—O— and

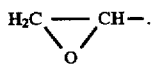

Compounds of Formulae III–VIII are described in U.S. Ser. No. 08/396,847; compounds of Formulae IX and X are described in U.S. Ser. No. 08/606,102.

The production of the compounds of formula I and of liquid crystalline mixtures containing these compounds is illustrated in more detail by the following Examples. C is a crystalline phase, S is a smectic phase, N is a nematic phase and I is the isotropic phase. Optical antipodes have in each case "mirror image properties", i.e. the same melting point, etc., but lead to opposite helical rotation and opposite circular polarization of reflected light.

EXAMPLE 1

0.44 g of N,N'-dicyclohexylcarbodiimide was added with 5 minutes, while stirring, to a solution of 0.1 g of (1R,2R)-trans-1,2-cyclohexanediol, 0.9 g of 4-(4-[8-acryloyloxyoctyloxy]-phenylcarbonyloxy)benzoic acid and 0.05 g of 4-(dimethylamino)-pyridine in 20 ml of dichloromethane. The reaction mixture was stirred overnight, filtered and the filtrate was concentrated. Chromatography of the residue on silica gel with hexane/ethyl acetate (vol. 8:2) and recrystallization from ethyl alcohol of the fractions, which were pure according to thin-layer chromatography, yielded 0.1 g of (1R,2R)-trans-1,2-bis[4-(4-[8-acryloyloxyoctyloxy]phenylcarbonyloxy) phenylcarbonyloxy]cyclohexane;

m.p. (C-I) 97° C.

The following compounds can be prepared in an analogous manner:

(1R,2R)-trans-1,2-bis [4-(5- [4-Acryloyloxybutyloxy] pyrimidin-2-yl)phenylcarbonyloxy]cyclohexane; m.p. (C-I) 107° C.;

(1R,2R)-trans-1,2-bis [2-(4- [4-acryloyloxybutyloxy]-phenyl)pyridin-5-yl)carbonyloxy]cyclohexane; m.p. (C-I) 108° C.;

(1R,2R)-trans-1,2-bis[4-(4-[6-acryloyloxyhexyloxy]-phenyl)cyclohexyl-ethylcarbonyloxy]cyclohexane; m.p. (C-I) 54° C.

There can also be prepared:

(1R,2R)-trans-1,2-bis [4-(4- [3-Acryloyloxypropyloxy]-phenylcarbonyloxy)phenylcarbonyloxy]cyclohexane;

(1R,2R)-trans-1,2-bis [4-(4- [4-acryloyloxybutoxy]-phenylcarbonyloxy)phenylcarbonyloxy]yclohexane;

(1R,2R)-trans-1,2-bis [4-(4- [5-acryloyloxypentyloxy]-phenylcarbonyloxy)phenylcarbonyloxy]cyclohexane;

(1R,2R)-trans-1,2-bis [4-(4- [6-acryloyloxyhexyloxy]-phenylcarbonyloxy)phenylcarbonyloxy]cyclohexane;

(1R,2R)-trans-1,2-bis [4-(4- [7-acryloyloxyheptyloxy]-phenylcarbonyloxy)phenylcarbonyloxy]cyclohexane;

(1R,2R)-trans-1,2-bis [4-(4- [9-acryloyloxynonyloxy]-phenylcarbonyloxy)phenylcarbonyloxy]cyclohexane;

(1R,2R)-trans-1,2-bis [4-(4-[10-acryloyloxydecyloxy]-phenylcarbonyloxy)phenylcarbonyloxy]cyclohexane;

(1R,2R)-trans-1,2-bis [4-(4-[11 -acryloyloxyundecyloxy]-phenylcarbonyloxy)phenylcarbonyloxy]cyclohexane;

(1R,2R)-trans-1,2-bis [4-(4-[12-acryloyloxydodecyloxy]-phenylcarbonyloxy)phenylcarbonyloxy]cyclohexane;

(1R,2R)-trans-1,2-bis(4-[3-acryloyloxypropyloxy]biphenyl-4'-carbonyloxy)cyclohexane;

(1R,2R)-trans-1,2-bis(4-[4-acryloyloxybutoxy]biphenyl-4'-carbonyloxy)cyclohexane;

(1R,2R)-trans-1,2-bis(4-[5-acryloyloxypentyloxy]biphenyl-4'-carbonyloxy)cyclohexane;

(1R,2R)-trans-1,2-bis(4-[6-acryloyloxyhexyloxy]biphenyl-4'-carbonyloxy)cyclohexane;

(1R,2R)-trans-1,2-bis(4-[7-acryloyloxyheptyloxy]biphenyl-4'-carbonyloxy)cyclohexane;

(1R,2R)-trans-1,2-bis(4-[8-acryloyloxyoctyloxy]biphenyl-4'-carbonyloxy)cyclohexane;

(1R,2R)-trans-1,2-bis(4-[9-acryloyloxynonyloxy]biphenyl-4'-carbonyloxy)cyclohexane;

(1R,2R)-trans-1,2-bis(4-[10-acryloyloxydecyloxy] biphenyl-4'-carbonyloxy)cyclohexane;
(1R,2R)-trans-1,2-bis(4-[11-acryloyloxyundecyloxy] biphenyl-4'-carbonyloxy)cyclohexane;
(1R,2R)-trans-1,2-bis(4-[12-acryloyloxydodecyloxy] biphenyl-4'-carbonyloxy)cyclohexane;
(1R,2R)-trans-1,2-bis [4-(5-[3-acryloyloxypropyloxy] pyrimidin-2-yl)phenylcarbonyloxy]cyclohexane;
(1R,2R)-trans-1,2-bis [4-(5-[5-acryloyloxypentyloxy]- pyrimidin-2-yl)phenylcarbonyloxy]cyclohexane;
(1R,2R)-trans-1,2-bis [4-(5-[6-acryloyloxyhexyloxy] pyrimidin-2-yl)phenylcarbonyloxy]cyclohexane;
(1R,2R)-trans-1,2-bis [4-(5-[7-acryloyloxyheptyloxy] pyrimidin-2-yl)phenylcarbonyloxy]cyclohexane;
(1R,2R)-trans-1,2-bis [4-(5-[8-acryloyloxyoctyloxy] pyrimidin-2-yl)phenylcarbonyloxy]cyclohexane;
(1R,2R)-trans-1,2-bis [4-(5-[9-acryloyloxynonyloxy] pyrimidin-2-yl)phenylcarbonyloxy]cyclohexane;
(1R,2R)-trans-1,2-bis [4-(5-[10-acryloyloxydecyloxy] pyrimidin-2-yl)phenylcarbonyloxy]cyclohexane;
(1R,2R)-trans-1,2-bis [4-(5-[11-acryloyloxyundecyloxy]- pyrimidin-2-yl)phenylcarbonyloxy]cyclohexane;
(1R,2R)-trans-1,2-bis [4-(5-[12-acryloyloxydodecyloxy]- pyrimidin-2-yl)phenylcarbonyloxy]cyclohexane;
(1R,2R)-trans-1,2-bis [4-(5-[3-acryloyloxypropyloxy] pyridin-2-yl)phenylcarbonyloxy]cyclohexane;
(1R,2R)-trans-1,2-bis [4-(5-[4-acryloyloxybutyloxy] pyridin-2-yl)phenylcarbonyloxy]cyclohexane;
(1R,2R)-trans-1,2-bis [4-(5-[5-acryloyloxypentyloxy] pyridin-2-yl)phenylcarbonyloxy]cyclohexane;
(1R,2R)-trans-1,2-bis [4-(5-[6-acryloyloxyhexyloxy] pyridin-2-yl)phenylcarbonyloxy]cyclohexane;
(1R,2R)-trans-1,2-bis [4-(5-[7-acryloyloxyheptyloxy] pyridin-2-yl)phenylcarbonyloxy]cyclohexane;
(1R,2R)-trans-1,2-bis [4-(5-[8-acryloyloxyoctyloxy] pyridin-2-yl)phenylcarbonyloxy]cyclohexane;
(1R,2R)-trans-1,2-bis [4-(5-[9-acryloyloxynonyloxy] pyridin-2-yl)phenylcarbonyloxy]cyclohexane;
(1R,2R)-trans-1,2-bis [4-(5-[10-acryloyloxydecyloxy] pyridin-2-yl)phenylcarbonyloxy]cyclohexane;
(1R,2R)-trans-1,2-bis [4-(5-[11-acryloyloxyundecyloxy] pyridin-2-yl)phenylcarbonyloxy]cyclohexane;
(1R,2R)-trans-1,2-bis [4-(5-[12-acryloyloxydodecyloxy] pyridin-2-yl)phenylcarbonyloxy]cyclohexane;
(1R,2R)-trans-1,2-bis [2-(4-[8-acryloyloxyoctyloxy]phenyl)- pyrimidin-5-ylcarbonyloxy]cyclohexane;
(1R,2R)-trans-1,2-bis [2-(4-[8-acryloyloxyoctyloxy]phenyl) -pyridin-5-ylcarbonyloxy]cyclohexane;
(1R,2R)-trans-1,2-bis [trans-4-(trans-4-[3- acryloyloxypropyl]cyclohexyl)cyclohexanecarbonyloxy] cyclohexane;
(1R,2R)-trans-1,2-bis [trans-4-(2-[trans-4-(3- acryloyloxypropyl)cyclohexyl]ethyl) cyclohexanecarbonyloxy]cyclohexane;
(1R,2R)-trans-1,2-bis [4-(trans-4-[3-acryloyloxypropyl]- cyclohexyl)phenylcarbonyloxy]cyclohexane; and
(1R,2R)-trans-1,2-bis [4-(2-[trans-4-(3-acryloyloxypropyl) cyclohexyl]ethyl) phenylcarbonyloxy]cyclohexane.

EXAMPLE 2

A solution of 0.2 g of (1R,2R)-trans-1,2-cyclohexanediol, 0.5 g of sodium hydride and 50 ml of tetrahydrofuran is stirred for 7 hours, treated with 1.1 g of 4-(5-[8- acryloyloxyoctyloxy]pyrimidin-2-yl)benzyl tosylate, the mixture is stirred at room temperature overnight, poured into 100 ml of water and then extracted three times with 50 ml of diethyl ether each time. The organic phases are combined, washed twice with 100 ml of water each time, dried over magnesium sulphate, filtered and the filtrate is concentrated. Chromatographic purification of the residue on silica gel with cyclohexane/ethyl acetate (vol. 8:2) and two-fold recrystallization from a cyclohexane/ethyl acetate mixture (vol. 8:2) of the fractions which are pure according to thin-layer chromatography gives 1.1 g of (1R,2R)-trans-1, 2-bis[4-(5-[8-acryloyloxyoctyloxy]pyrimidin-2-yl) benzyloxy]cyclohexane.

The following compounds can be prepared in an analogous manner:
(1R,2R)-trans-1,2-bis [4-(4-[3-Acryloyloxypropyloxy]- phenylcarbonyloxy)benzyloxy]cyclohexane;
(1R,2R)-trans-1,2-bis [4-(4-[4-acryloyloxybutoxy]- phenylcarbonyloxy)benzyloxy]cyclohexane;
(1R,2R)-trans-1,2-bis [4-(4-[5-acryloyloxypentyloxy]- phenylcarbonyloxy)benzyloxy]cyclohexane;
(1R,2R)-trans-1,2-bis [4-(4-[6-acryloyloxyhexyloxy] phenylcarbonyloxy)benzyloxy]cyclohexane;
(1R,2R)-trans-1,2-bis [4-(4-[7-acryloyloxyheptyloxy]- phenylcarbonyloxy)benzyloxy]cyclohexane;
(1R,2R)-trans-1,2-bis [4-(4-[9-acryloyloxynonyloxy] phenylcarbonyloxy)benzyloxy]cyclohexane;
(1R,2R)-trans-1,2-bis [4-(4-[10-acryloyloxydecyloxy]- phenylcarbonyloxy)benzyloxy]cyclohexane;
(1R,2R)-trans-1,2-bis [4-(4-[11-acryloyloxyundecyloxy]- phenylcarbonyloxy)benzyloxy]cyclohexane;
(1R,2R)-trans-1,2-bis [4-(4-[12-acryloyloxydodecyloxy]- phenylcarbonyloxy)benzyloxy]cyclohexane;
(1R,2R)-trans-1,2-bis(4-[3-acryloyloxypropyloxy]biphenyl- 4'-methoxy)cyclohexane;
(1R,2R)-trans-1,2-bis(4-[4-acryloyloxybutoxy]biphenyl-4'- methoxy) cyclohexane;
(1R,2R)-trans-1,2-bis(4-[5-acryloyloxypentyloxy]biphenyl- 4'-methoxy)cyclohexane;
(1R,2R)-trans-1,2-bis(4-[6-acryloyloxyhexyloxy]biphenyl- 4'-methoxy)cyclohexane;
(1R,2R)-trans-1,2-bis(4-[7-acryloyloxyheptyloxy]biphenyl- 4'-methoxy)cyclohexane;
(1R,2R)-trans-1,2-bis(4-[9-acryloyloxynonyloxy]biphenyl- 4'-methoxy)cyclohexane;
(1R,2R)-trans-1,2-bis(4-[10-acryloyloxydecyloxy] biphenyl-4'-methoxy)cyclohexane;
(1R,2R)-trans-1,2-bis(4-[11-acryloyloxyundecyloxy] biphenyl-4'-methoxy)cyclohexane;
(1R,2R)-trans-1,2-bis(4-[12-acryloyloxydodecyloxy] biphenyl-4'-methoxy)cyclohexane;
(1R,2R)-trans-1,2-bis [4-(5-[3-acryloyloxypropyloxy] pyrimidin-2-yl)benzyloxy]cyclohexane;
(1R,2R)-trans-1,2-bis [4-(5-[4-acryloyloxybutyloxy] pyrimidin-2-yl)benzyloxy]cyclohexane;
(1R,2R)-trans-1,2-bis [4-(5-[5-acryloyloxypentyloxy] pyrimidin-2-yl)benzyloxy]cyclohexane;
(1R,2R)-trans-1,2-bis [4-(5-[6-acryloyloxyhexyloxy] pyrimidin-2-yl)benzyloxy]cyclohexane;
(1R,2R)-trans-1,2-bis [4-(5-[7-acryloyloxyheptyloxy] pyrimidin-2-yl)benzyloxy]cyclohexane;
(1R,2R)-trans-1,2-bis [4-(5-[8-acryloyloxyoctyloxy] pyrimidin-2-yl)benzyloxy]cyclohexane;
(1R,2R)-trans-1,2-bis [4-(5-[9-acryloyloxynonyloxy] pyrimidin-2-yl)benzyloxy]cyclohexane;
(1R,2R)-trans-1,2-bis [4-(5-[10-acryloyloxydecyloxy] pyrimidin-2-yl)benzyloxy]cyclohexane;
(1R,2R)-trans-1,2-bis [4-(5-[11-acryloyloxyundecyloxy] pyrimidin-2-yl)benzyloxy]cyclohexane;
(1R,2R)-trans-1,2-bis [4-(5-[12-acryloyloxydodecyloxy] pyrimidin-2-yl)benzyloxy]cyclohexane;

(1R,2R)-trans-1,2-bis [4-(5-[3-acryloyloxypropyloxy] pyridin-2-yl)benzyloxy]cyclohexane;
(1R,2R)-trans-1,2-bis [4-(5-[4-acryloyloxybutyloxy] pyridin-2-yl)benzyloxy]cyclohexane;
(1R,2R)-trans-1,2-bis [4-(5-[5-acryloyloxypentyloxy] pyridin-2-yl)benzyloxy]cyclohexane;
(1R,2R)-trans-1,2-bis [4-(5-[6-acryloyloxyhexyloxy] pyridin-2-yl)benzyloxy]cyclohexane;
(1R,2R)-trans-1,2-bis [4-(5-[7-acryloyloxyheptyloxy] pyridin-2-yl)benzyloxy]cyclohexane;
(1R,2R)-trans-1,2-bis [4-(5-[8-acryloyloxyoctyloxy] pyridin-2-yl)benzyloxy]cyclohexane;
(1R,2R)-trans-1,2-bis [4-(5-[9-acryloyloxynonyloxy] pyridin-2-yl)benzyloxy]cyclohexane;
(1R,2R)-trans-1,2-bis [4-(5-[10-acryloyloxydecyloxy] pyridin-2-yl)benzyloxy]cyclohexane;
(1R,2R)-trans-1,2-bis [4-(5-[11-acryloyloxyundecyloxy] pyridin-2-yl)benzyloxy]cyclohexane;
(1R,2R)-trans-1,2-bis [4-(5-[12-acryloyloxydodecyloxy] pyridin-2-yl)benzyloxy]cyclohexane;
(1R,2R)-trans-1,2-bis [(2-[4-(8-acryloyloxyoctyloxy)-phenyl]pyrimidin-5-yl)methoxy]cyclohexane;
(1R,2R)-trans-1,2-bis [(trans-4-(trans-4-[3-acryloyloxypropyl]cyclohexyl)cyclohexyl)methoxy] cyclohexane;
(1R,2R)-trans-1,2-bis [(trans-4-[2-(trans-4-[3-acryloyloxypropyl]cyclohexyl)ethyl]cyclohexyl) methoxy]cyclohexane;
(1R,2R)-trans-1,2-bis [4-(trans-4-[3-acryloyloxypropyl]-cyclohexyl)benzyloxy]cyclohexane; and
(1R,2R)-trans-1,2-bis [4-(2-[trans-4-(3-acryloyloxypropyl) cyclohexyl]ethyl)benzyloxy]cyclohexane.

I claim:
1. A compound of the general formula

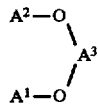

wherein
$A^1$ and $A^2$ each are a cross-linkable mesogenic residue; and
$A^3$ is (R,R)- or (S,S)-trans-1,2-cyclohexyl-diyl.

2. The compound of claim 1, wherein the mesogenic residues $A^1$ and $A^2$ each are a residue of general formula II

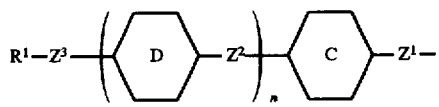

wherein
rings C and D each independently are selected from the groups consisting of pyridine-2,5-diyl, pyrimidine-2,5-diyl, trans-1,4-cyclohexylene, trans-1,3-dioxane-2,5-diyl, 1,4-phenylene, and 1,4-phenylene substituted with one or more halogen, methyl or cyano;
$Z^1$ is selected from the group consisting of $(CH_2)_m$—, —CO—, —$(CH_2)_m$CO— and —$(CH_2)_m$OOC—;
$Z^2$ is selected from the group consisting of a single bond, —$CH_2CH_2$—, —$CH_2O$—, —$OCH_2$—, —COO—, —OOC—, —$(CH_2)_4$—, —$O(CH_2)_3$— and —$(CH_2)_3O$—;
$Z^3$ is selected from the group consisting of —$(CY_2)_m$—, —$O(CY_2)_m$—, —$(CY_2)_m O$—, —$(CY_2)_m COO$—, —$(CY_2)_m OOC$—, —$(Si[(CH_3)_2]O)_m$—, —$OCH_2(Si[(CH_3)_2]O)_m Si[(CH_3)_2]CH_2O$— and —$NHCH_2(Si[(CH_3)_2]O)_m Si[(CH_3)_2]CH_2NH$—;

Y is hydrogen or fluorine;
n is 0, 1 or 2;
m is a whole number of 1 to 16; and
$R^1$ is a cross-linkable group selected from the group consisting of $CH_2$=CH—, $CH_2$=CH—COO—, $CH_2$=C($CH_3$)—COO—, $CH_2$=C(Cl)—COO—, $CH_2$=C(Ph)—COO—, $CH_2$=CH—COO—Ph—, $CH_2$=CH—CO—NH—, $CH_2$=C($CH_3$)—CONH—, $CH_2$=C(Cl)—CONH—, $CH_2$=C(Ph)—CONH—, $CH_2$=C(COOR')—$CH_2$—COO—, $CH_2$=CH—O—, $CH_2$=CH—OOC—, Ph—CH=CH—, $CH_3$—C(=NR')—, cis,trans HOO—CR'=CR'—COO—,

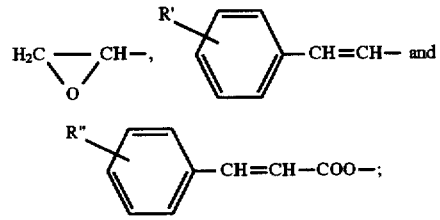

Ph is phenyl;
R' is lower alkyl; and
R" is selected from the group consisting of methyl, methoxy, cyano and halogen;
wherein $R^1$—$Z^3$— contains no —O—O— or —N—O— groups.

3. The compound of claim 2, wherein
$Z^1$ is selected from the group consisting of —$(CH_2)$—, —CO—, —$(CH_2)_3$— and —$(CH_2)_2CO$—; and
n is 0 or 1.

4. The compound of claim 3, wherein the mesogenic residues $A^1$ and $A^2$ are the same.

5. The compound of claim 4, wherein the residues $A^1$ and $A^2$ consist of a residue of the formula

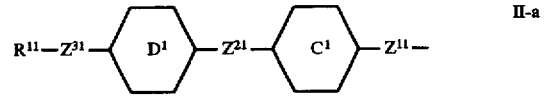

II-a wherein
rings $C^1$ and $D^1$ each independently are selected from the group consisting of pyridine-2,5-diyl, pyrimidine-2,5-diyl, trans-1,4-cyclohexylene, 1,4-phenylene, and 1-4 phenylene substituted with fluorine;
$Z^{11}$ is —$CH_2$— or —CO—;
$Z^{21}$ is selected from the group consisting of a single bond, —$CH_2O$—, —COO— and —OOC—;
$Z^{31}$ is selected from the group consisting of —$(CH_2)_{m'}$—, —$(CH_2)_{m'}$·O—, —$(CH_2)_{m'}$·COO— and —$(CH_2)_{m'}$OOC—;
m' is a whole number of 3 to 12; and
$R^{11}$ is selected from the group consisting of $CH_2$=CH—COO—, $CH_2$=C($CH_3$)—COO—, $CH_2$=CH—O— and

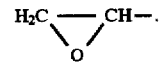

6. The compound of claim 5 selected from the group consisting of the formulae

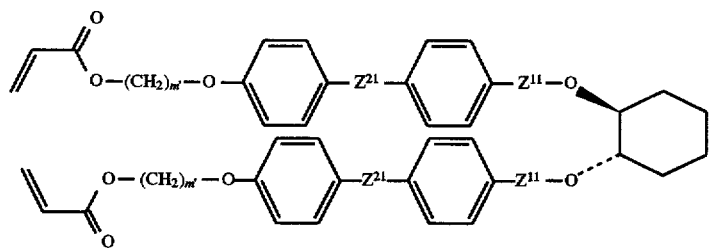

I-A

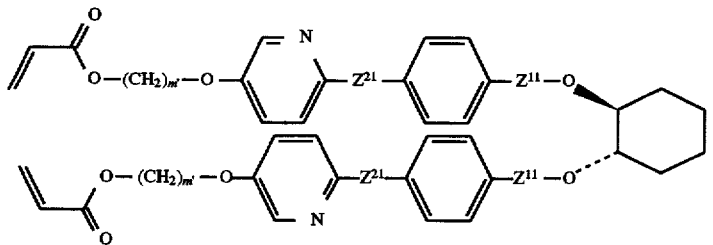

I-B

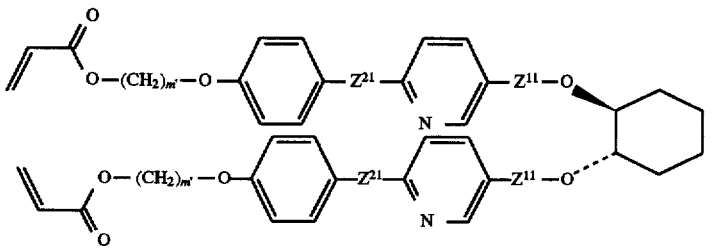

I-C

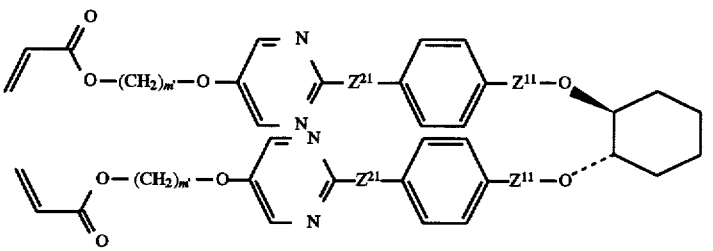

I-D

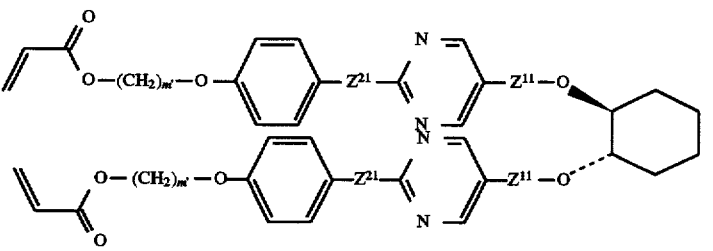

I-E and the enantiomers thereof, wherein $Z^{11}$ is —CO—; $Z^{21}$ is a single bond or —COO—; and m' is a whole number of 3 to 12.

7. The compound of claim 6, wherein $Z^{21}$ is —COO—.

8. A mixture consisting of photo-cross-linkable liquid crystalline compounds comprising a compound of formula I, claim 1.

9. The liquid crystalline mixture of claim 8, further comprising a compound selected from the group of formulae consisting of

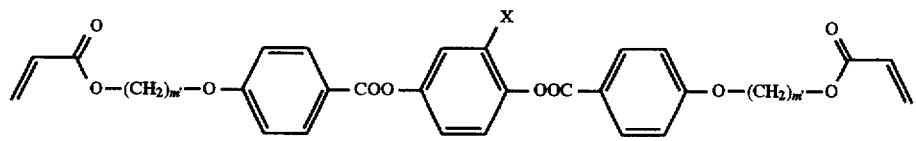

III

-continued
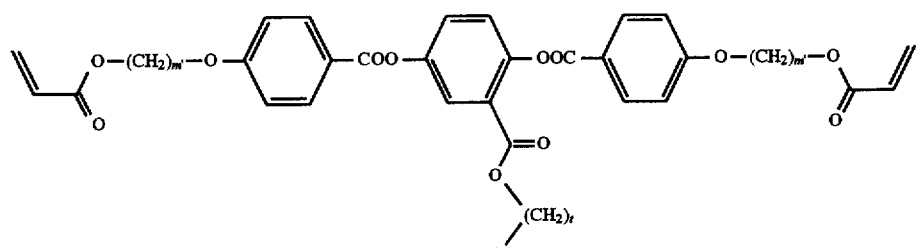
IV
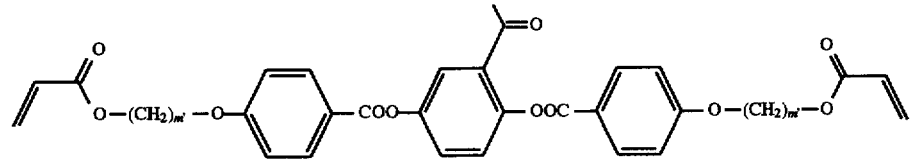
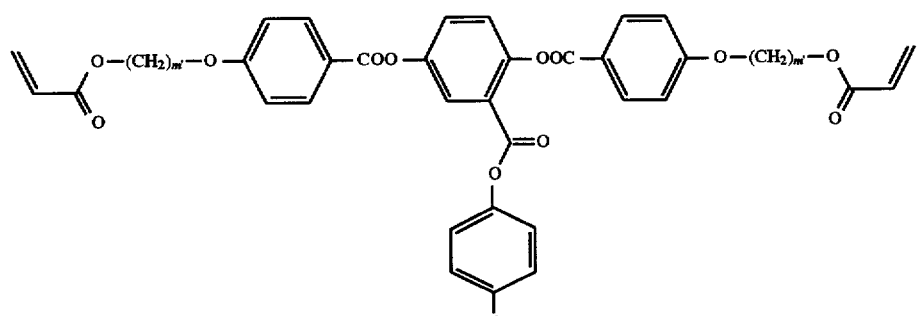
V
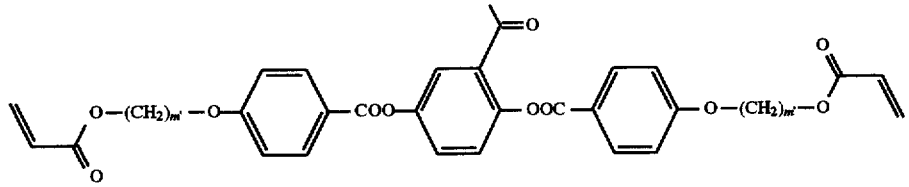
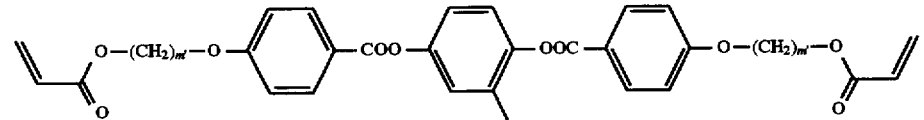
VI
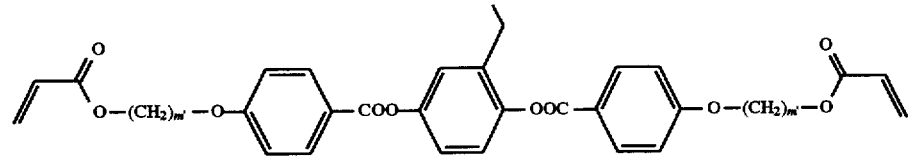

VII

VIII

IX and

X wherein

X is selected from the group consisting of hydrogen, fluorine, chlorine, bromine and methyl;

m' is a whole number of 3 to 12;

t is a whole number of 2 to 12;

Z is —OCH₂— or —OOC—;

A is 1,4-phenylene or 2-or 3-fluoro-1,4-phenylene;

S is —(CH₂)_{m'}—; —(CH₂)_{m'}O— or —O(CH₂)_{m'}—; and

R is selected from the group consisting of CH₂=CH—COO—, CH₂=C(CH₃)—COO—, CH₂=CH—O— and

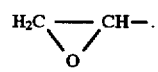

10. The compound of claim 2, selected from the group consisting of 0.1 g of (1R,2R)-trans-1,2-bis[4-(4-[8-acryloyloxyoctyloxy]phenylcarbonyloxy) phenylcarbonyloxy]cyclohexane;

(1R,2R)-trans-1,2-bis [4-(5-[4-Acryloyloxybutyloxy] pyrimidin-2-yl)phenylcarbonyloxy]cyclohexane;

(1R,2R)-trans-1,2-bis [2-(4-[4-acryloyloxybutyloxy]-phenyl)pyridin-5-yl)carbonyloxy]cyclohexane; and (1R,2R)-trans-1,2-bis [4-(4-[6-acryloyloxyhexyloxy]-phenyl)cyclohexyl-ethylcarbonyloxy]cyclohexane.

* * * * *